United States Patent [19]

Moore

[11] 4,086,914
[45] May 2, 1978

[54] IMPLANT INJECTOR

[76] Inventor: Edwin Bailey Moore, 10214 Willowgrove, Houston, Tex. 77035

[21] Appl. No.: 767,979

[22] Filed: Feb. 11, 1977

[51] Int. Cl.² .............................................. A61N 5/00
[52] U.S. Cl. ..................................... 128/1.2; 128/217; 128/264; 221/4
[58] Field of Search ................ 128/1.2, 1.1, 217, 264; 221/2, 4, 279

[56] References Cited

U.S. PATENT DOCUMENTS

| | | | |
|---|---|---|---|
| 2,086,580 | 7/1937 | Shirley | 128/264 |
| 2,269,963 | 1/1942 | Wappler | 221/2 X |
| 2,885,110 | 5/1959 | Tregilgas | 221/2 |
| 3,674,006 | 7/1972 | Holmer | 128/1.2 |

OTHER PUBLICATIONS

*Medical Journ. and Record,* 1925 (Jul.–Dec.) pp. 527–529.

*Primary Examiner*—Kyle L. Howell
*Attorney, Agent, or Firm*—Ranseler O. Wyatt

[57] ABSTRACT

An implant injector having means for deposit of spaced implants wherein an inner housing member receives an outer housing member and a continuous channel is formed in the outer surface of the inner member, and the outer member has an inwardly projecting stud adapted to be received in said channel, said channel extending longitudinally of said inner member in spaced, connecting horizontal semicircular steps, which permit a plunger carried by said outer member to be moved in spaced advances as said outer member is actuated, moving an implant out of said inner member upon each forward movement of said plunger in said inner member.

4 Claims, 6 Drawing Figures

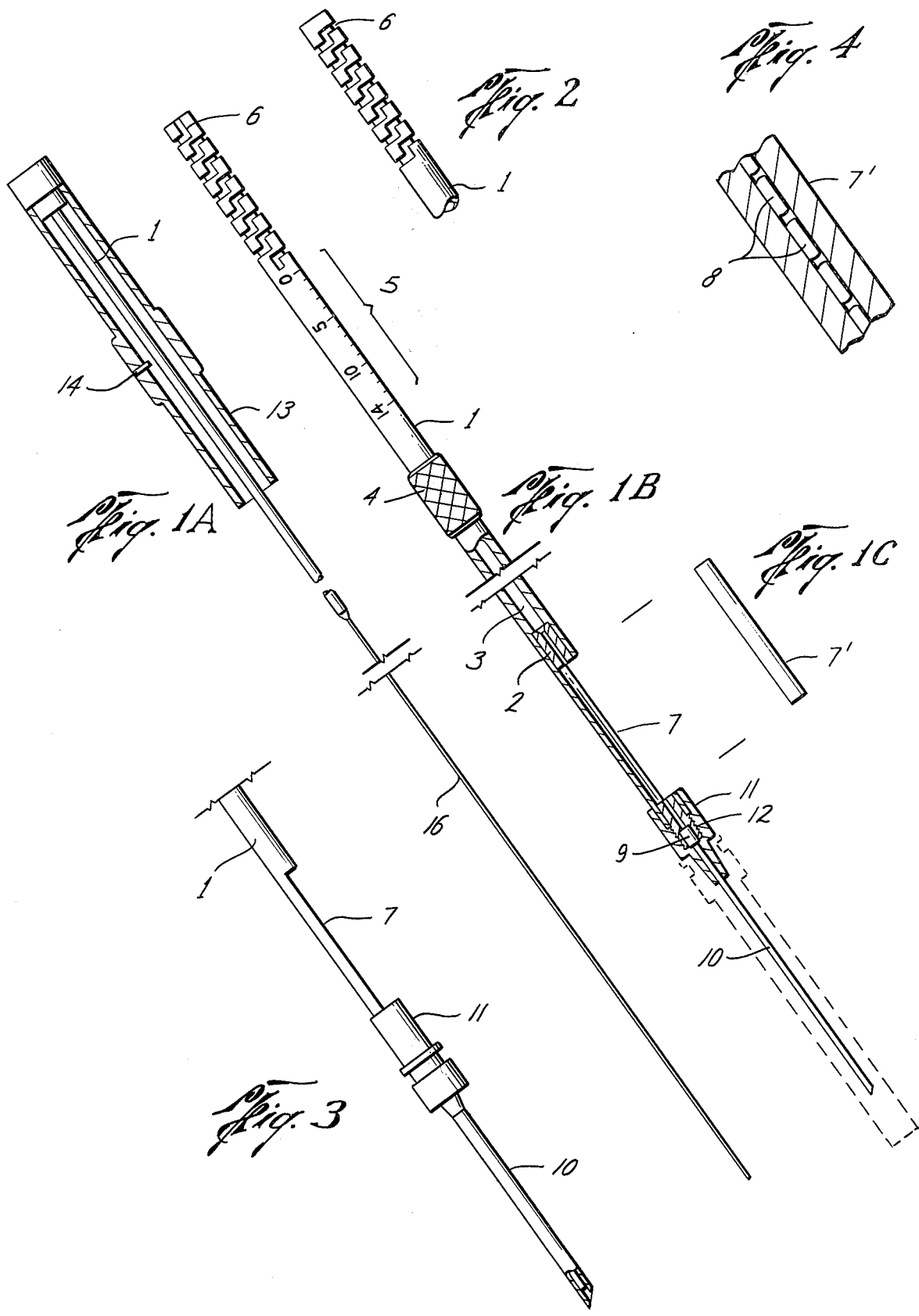

IMPLANT INJECTOR

BACKGROUND OF THE INVENTION

In depositing implants, such as the radio-active gold implants for the treatment of cancer, and the like, it is important that the implants be deposited in spaced intervals and that the user of the implant mechanism be constantly advised of the number of implants deposited as the process progresses. It is an object of this invention to provide an accurately calibrated implant injector that will provide a measured movement of the plunger which moves the implant into the tissue and assures the deposit of a single implant with each rotation of the outer member.

SUMMARY OF THE INVENTION

An implant injector having an inner and an outer member and a plunger on the outer member traveling within the inner member, adapted to deposit an implant from the inner member upon each forward movement of said plunger, a continuous channel formed longitudinally in the outer surface of said inner member and an inwardly projecting stud in said outer member is adapted to ride in said channel, said channel being formed in spaced, connected, semi-circular steps, the space between each step being equal to the length of each implant.

BRIEF DESCRIPTION OF THE DRAWING

FIG. 1A is an elevational view of the outer member, partially in cross section.

FIG. 1B is an elevational view of the inner member, partially in cross section.

FIG. 1C is an elevational view of the implant cartridge.

FIG. 2 is a partial view of the inner member, showing the reverse area of that shown in FIG. 1B.

FIG. 3 is a partial view of the inner member, and

FIG. 4 is a fragmentary view, in cross section, of the implant cartridge.

DESCRIPTION OF THE PREFERRED EMBODIMENT

In the drawing the numeral 1 designates the inner member, which has a horizontal passageway therethrough as 2, which is enlarged in the upper area as at 3. A knurled sleeve 4 is formed on the outer surface of the inner member, which provides a hand grip for the user. Graduate indicia 5 is engraved on the outer surface of the upper portion of the inner member, and a continuous longitudinal channel 6 is formed in the outer surface of the inner member and is divided into spaced horizontal connecting semi-circular steps, the distance between each step corresponding with the distance between each graduate indicia.

In the lower portion of the inner member is a cartridge receiving chamber, 7, adapted to receive the cartridge 7' in which the implants, as 8, 8, are stored in the passageway therethrough, which, when the cartridge is mounted in the chamber 7, is in alignment with the passageway 2 in the inner member. The inner member 1 terminates in a needle receiving chamber 9 in which the top of the needle 10 is received and the retainer 11 is internally threaded to mesh with the external threads 12 of the inner member to lock the needle 10 in place.

The outer member has the jacket 13 in which the inwardly projecting stud 14 is mounted, and which has the axial member 15 terminating in the plunger 16 which is adapted to fit in the passageway 3 of the inner member 1. A cap 17 may be mounted on the retainer 11 to protect the needle 10 when the device is not in use.

As the plunger is inserted into the inner member, the projection 14 will abut against the upper end of the inner member, and the lower end of the jacket 13 will be in alignment with the indicia 0, and the extended end of the plunger 16 will have contacted the implants in the cartridge and moved them through the passageway 2, and through the hollow needle to the end thereof. The needle is then inserted into the area where the implants are to be deposited, and the jacket is moved forward on the inner member to the first semi-circle where the stud 14 will stop the forward movement of the outer member. This movement will move the first implant out of the needle and into the area where it is to be deposited. The needle is withdrawn far enough to allow another implant, and the jacket 13 is rotated, the stud 14 traveling around the semi-circle to the next connecting channel, and the plunger moved forward as the jacket is moved to the next semi-circle, and this forward movement of the plunger will move another implant out of the needle into the area where it is to be deposited. This procedure continues until the desired amount of implants have been deposited.

The operator at all times will be advised of the number of implants deposited by the indicia, the length of each connecting channel between each circular step being calibrated to correspond to the length of each implant and the distance between the respective graduates of the indicia.

To reload the unit, the outer member is rotated in reverse and backed off of the inner member, and the plunger withdrawn, clearing the cartridge 7' which may then be removed and resupplied with implants.

It is intended that the cartridge will hold fourteen implants, in as much as that is the calibrated numbers shown. Of course, any number of implants may be used as desired, so long as the number of implants correspond with the number of steps formed in the outer surface of the inner housing member.

The channel having the semi-circular steps is shown formed in the inner housing, however, it is contemplated that said channel may also be formed in the inner wall of the outer housing, and the stud that travels in this channel, mounted in the outer wall of the inner housing.

What I claim is:

1. In an implant injector having inner and outer members, said inner member having an axial passageway therethrough, a plunger on the outer member adapted to pass through said axial passageway of the inner member, a continuous channel in the surface of one of said members, divided into spaced, connecting semi-circular steps, means mounted in the other member adapted to be received and to travel in said channel as the plunger is moved through the inner member against implants therein.

2. The device defined in claim 1 wherein said semi-circular steps are separated from each other a distance calibrated with the lengths of each implant.

3. The device defined in claim 1 wherein indicia is formed on the inner member, calibrated with the longitudinal movement of said plunger, and a jacket on said outer member receives the upper end of said inner member, the lower end of said jacket covering one graduate of said indicia with each step of forward movement of said plunger.

4. The device defined in claim 1 wherein said outer member has a jacket on one end which fits over said inner member, and said means to be received by said channel on said inner member, projects inwardly from said jacket.

* * * * *